United States Patent [19]

Tomie

[11] Patent Number: 5,569,916
[45] Date of Patent: Oct. 29, 1996

[54] ELECTRON SPECTROSCOPY APPARATUS

[75] Inventor: Toshihisa Tomie, Tsukuba, Japan

[73] Assignee: Agency of Industrial Science & Technology, Ministry of International Trade & Industry, Tokyo, Japan

[21] Appl. No.: 380,694

[22] Filed: Jan. 30, 1995

Related U.S. Application Data

[63] Continuation-in-part of Ser. No. 87,901, Jul. 9, 1993, abandoned.

[30] Foreign Application Priority Data

Jul. 9, 1992  [JP]  Japan ................................. 4-205954

[51] Int. Cl.$^6$ ................................................ H01J 37/00
[52] U.S. Cl. .................... 250/287; 250/305; 250/310; 378/43
[58] Field of Search ................................. 250/305, 310, 250/492.1, 287; 378/34, 43, 119

[56] References Cited

U.S. PATENT DOCUMENTS

| | | | |
|---|---|---|---|
| 3,826,996 | 7/1974 | Jaegle et al. | 331/94.5 |
| 4,229,708 | 10/1980 | Mani et al. | 372/5 |
| 4,255,656 | 3/1981 | Barrie et al. | 250/305 |
| 4,435,828 | 3/1984 | Epstein et al. | |
| 4,484,339 | 11/1984 | Mullozzi et al. | 378/82 |
| 4,486,659 | 12/1984 | Turner | 250/306 |
| 4,680,467 | 7/1987 | Bryson | 250/305 |
| 4,771,430 | 9/1988 | Suckewe et al. | 372/5 |
| 4,896,341 | 1/1990 | Forsyth et al. | 378/34 |
| 5,022,064 | 6/1991 | Iketaki | 378/145 |
| 5,132,994 | 7/1992 | Kato | 378/43 |
| 5,148,462 | 9/1992 | Spitsyn et al. | 378/143 |
| 5,175,757 | 12/1992 | Augustoni et al. | 378/145 |
| 5,450,463 | 9/1995 | Iketaki | 378/43 |

FOREIGN PATENT DOCUMENTS 0350874  1/1990  European Pat. Off. .

OTHER PUBLICATIONS

Nuclear Instruments and Methods, vol. 208, 1983, pp. 735–752, B. Sonntag, "Photoemission from Atoms and Molecules".

Appl. Phys. Lett., vol. 56, No. 19, May 7, 1990, Harald Ade, et al., "X–Ray Spectromicroscopy with a Zone Plate Generated Microphobe".

Primary Examiner—Bruce C. Anderson
Attorney, Agent, or Firm—Oblon, Spivak, McClelland, Maier & Neustadt, P.C.

[57] ABSTRACT

An electron spectroscopy apparatus in which pulses of EUV of a prescribed wavelength are generated from plasma produced by pulsed laser beam irradiation of a target containing specific elements, the EUV pulses are used to irradiate a specimen, producing an emission of photoelectrons from the specimen, and the time it takes these photoelectrons to pass along a flight channel is measured and analyzed.

14 Claims, 3 Drawing Sheets

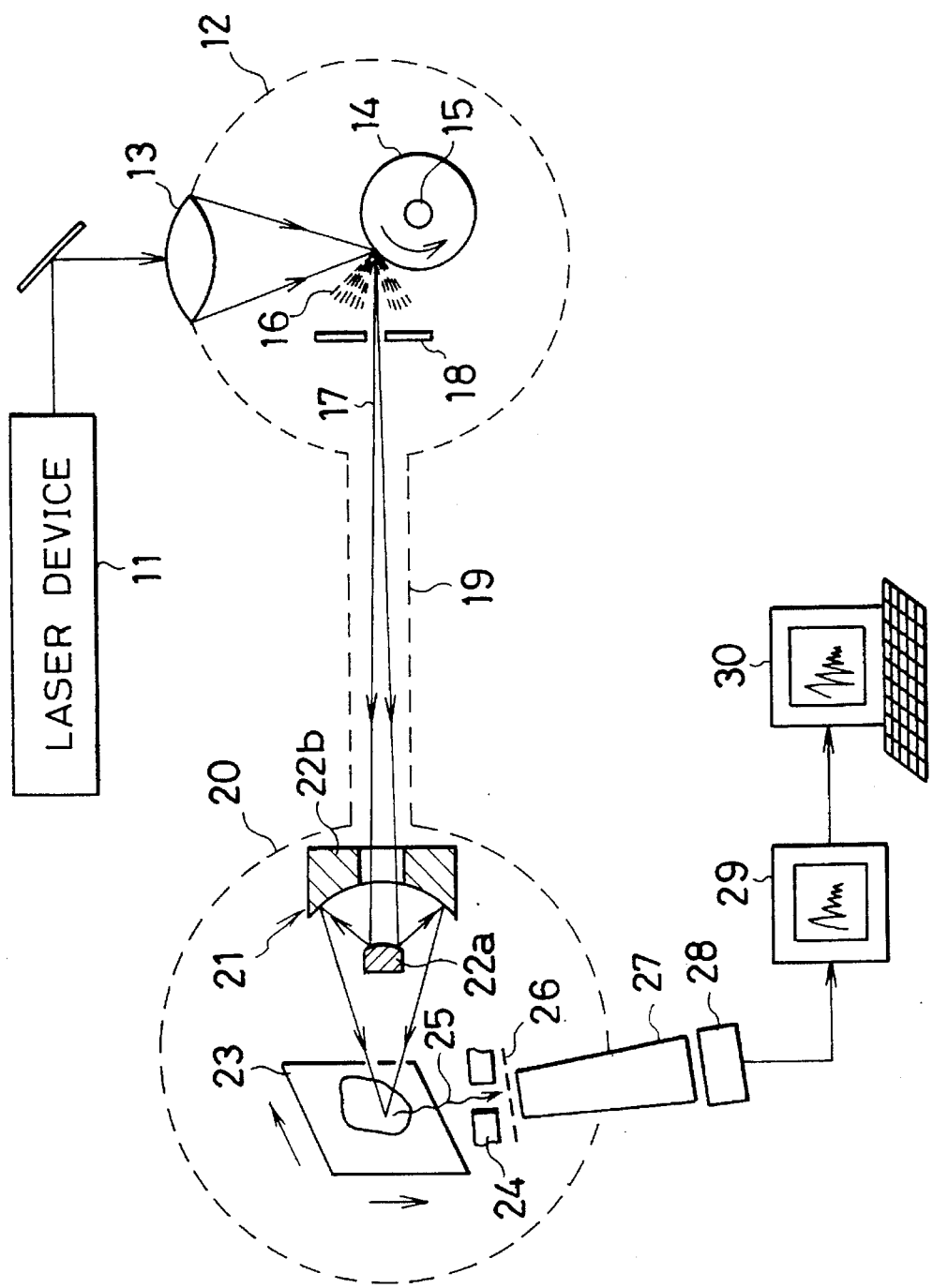

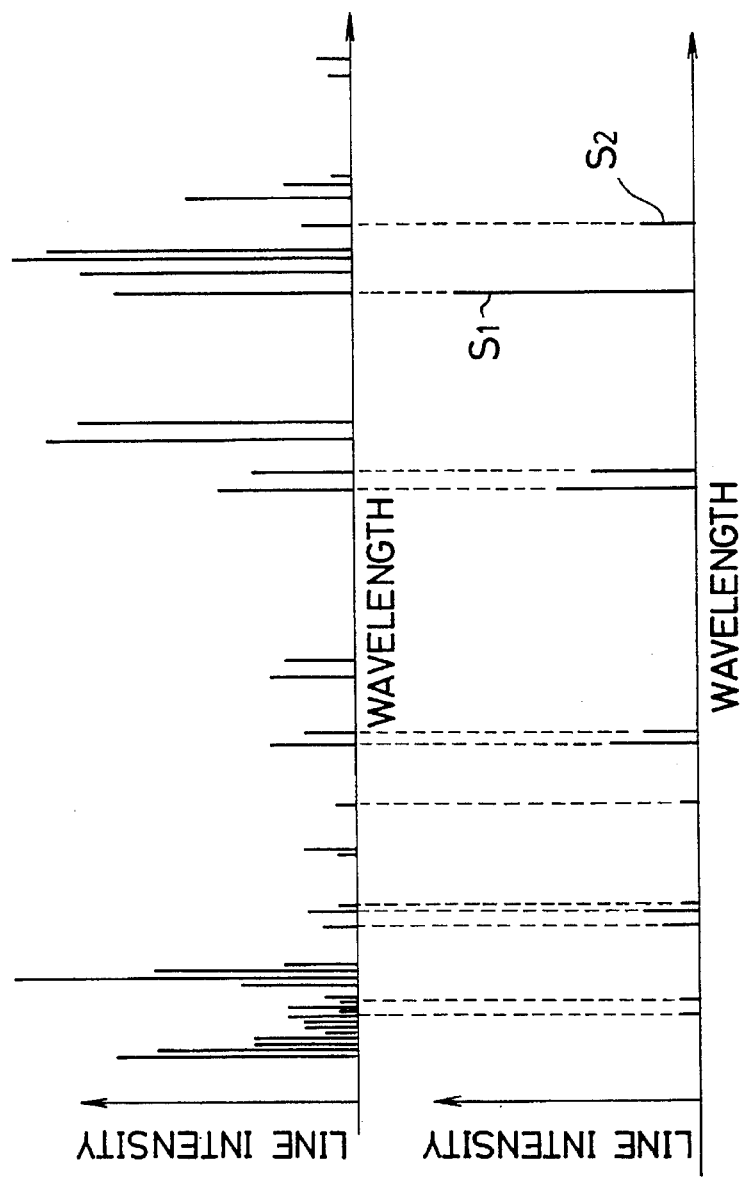
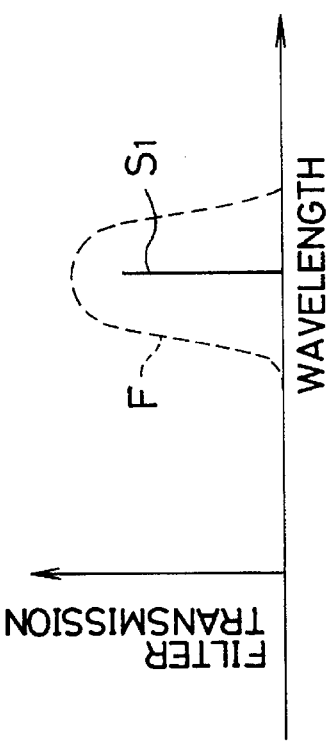
FIG.3(a)
FIG.3(b)
FIG.3(c)

ELECTRON SPECTROSCOPY APPARATUS

CROSS-REFERENCE TO RELATED APPLICATION

This is a continuation-in-part of application Ser. No. 08/087,901, filed Jul. 9, 1993, abandoned.

BACKGROUND OF THE INVENTION

1. Field of the Invention

This invention relates to an electron spectroscopy apparatus that can obtain information relating to the chemical state of elements in a specimen by analyzing the energy spectrum of photoelectrons generated when the specimen is irradiated, for example by EUV (extreme ultraviolet rays).

2. Description of the Prior Art

Irradiating a substance with visible light, EUV, X-rays, electrons or the like causes ejection of electrons from the substance. The energy distribution of these ejected electrons contains information relating to the state of the substance. Auger electron spectroscopy which measures Auger electrons generated by electron beam radiation, and photoelectron spectroscopy which measures photoelectrons generated by EUV or X-ray radiation, are important analytical techniques in research relating to the state of substances, especially the surface state. Photoelectron spectroscopy is the more important of these techniques.

Photoelectron spectroscopy will now be explained with reference to FIG. 1. When X-ray 2 having a photon energy $E_X$ impinge on a target specimen 1, electrons 3 in the specimen 1 are excited by receiving the energy from the X-ray 2, whereby the X-ray 2 are thus absorbed. If the photon energy $E_X$ of the X-ray 2 is greater than the binding energy $E_B$ of the electrons 3, electrons 3 are discharged from the specimen 1 as photoelectrons 4 with an energy of $E_p = E_X - E_B$. The basic principle of photoelectron spectroscopy is that in the case of X-ray the beam can be monochromatic, and as photon energy $E_X$ can be known with a high degree of precision, the binding energy $E_B$ of electrons 3 in the specimen 1 can be established with a high degree of resolution by measuring with high precision the energy $E_p$ of the photoelectrons 4. As photoelectrons 4 outside the specimen 1 are released from the outermost surface layer, they can provide information about the state of the surface. With the advances being made in the development of thin-film devices and surface functions therefore becoming increasingly important, information relating to surfaces is also becoming more and more important.

Compared with Auger electron spectroscopy, the advantageous features of X-ray photoelectron spectroscopy are that as it offers a higher energy resolution it can therefore provide much more detailed information, it does little damage to the specimen, and it can be used to observe insulators. A drawback of X-ray photoelectron spectroscopy has been its low spatial resolution. Generally speaking, specimens are spatially non-uniform and have to be analyzed at the microscopic level. With process technologies dealing with ever finer dimensions, microanalysis is becoming increasingly necessary.

Advances have been made with research and development related to obtaining spatially-resolved photoelectron spectra, and have led to the development of a direct imaging technique in which a photoelectron image is magnified and a scanning technique in which spatial distribution is obtained by scanning a location on the specimen with a tightly focused X-ray beam.

The difficulty of focusing X-rays gave rise to the direct imaging method. In U.S. Pat. No. 4,680,467, for example, X-rays of 1,487 eV are focused into a large diameter of 100 to 600 μm using a crystal spectroscope. Thus, this prior art presents a need for a process for electrostatically or magnetostatically enlarging the image of spatial distribution of photoelectrons produced from a relatively large region irradiated by the X-rays in order to obtain detailed spatial distribution of photoelectrons. Progress has proceeded to the point at which, with an X-ray tube as the X-ray source and using an electrostatic lens, the spatial distribution of photoelectrons has been measured with a resolution of 20 μm (P. Coxon et al., J. Elect. Spectrosc. and Rel. Phenom. 52 821 (1990)), and lines of 25 μm width have been observed with synchrotron radiation as the X-ray source and using a magnetic field to produce enlarged photoelectron images (P. Pianetta et al., J. Elect. Spectrosc. and Rel. Phenom. 52 797 (1990)).

Although the direct imaging method has achieved a spatial resolution to some extent, it is very difficult for such method to achieve a sub-micron resolution which is strongly needed in today's research. On the other hand, EUV optic device technology has recently advanced to the point where EUV having a wavelength of several nanometers (several hundreds of eV in photon energy) can be focused down to a beam just several tens of nanometers in diameter, thereby making it possible to use a method for focusing EUV and scanning the focused EUV with an optic device to obtain photoelectron spectroscopy with a sufficiently high resolution. However, it is not easy to emit intensive EUV from an X-ray tube which has heretofore been used as an X-ray source. With an undulator beam which is now an ultra-highly intensive light source of a synchrotron radiation facility as the EUV source and a zone plate or Schwarzschild optics to concentrate the beam, photoelectron images have been obtained with a spatial resolution of up to 0.3 μm (H. Ade et al., Appl. Phys. Lett. 56 1841 (1990)). Photoelectron microscopes are attracting attention as one of the most promising undulator beam applications, and is an area in which research is expected to make considerable progress.

However, using an undulator beam as the EUV source presents a major obstacle to wider use of the minute analysis photoelectron microscopy. This is because the facility is quite bulky and costly, the beam cannot be easily switched on and off, so that in order to use the facility efficiently it has to be used continuously throughout the day, and it requires special operators. These reasons put upkeep of a synchrotron facility beyond the capacity of a small-scale user group.

Moreover, even with an undulator beam, photoelectron spectroscopy of intermittent phenomena is difficult. One example is photoelectron spectroscopy of clusters. A cluster is a molecular compound having a state that is midway between molecular and solid. Research into the properties of clusters is not only highly interesting from the academic point of view but also has the potential of giving rise to new applications, and it is for this reason that cluster research is attracting attention. Virtually all clusters are intermittently produced in very small quantities, for example by irradiating a solid with a pulsed laser beam. Because clusters are produced intermittently, only quite a small fraction of time of the continuously emitting undulator beam is utilized for the measurement. Also, time-of-flight spectroscopy, which is capable of detecting photoelectrons with a very high efficiency, cannot be employed with the continuous irradiation of an undulator X-ray source.

The principal object of this invention is therefore to provide a compact, high-efficiency electron spectroscopy apparatus that is capable of performing high spatial resolution measurements in a short data acquisition time.

A further object of the invention is to provide an electron spectroscopy apparatus that can effectively perform photoelectron spectroscopy of intermittent phenomena such as in cluster observation.

SUMMARY OF THE INVENTION

In accordance with the present invention, this object is attained by an electron spectroscopy apparatus comprising means for generating EUV pulses using a laser plasma composed mainly of a single ion species produced by the irradiation of a pulsed laser beam on a solid target containing a specific element, the single ion species emitting EUV pulses of a plurality of spectrally well-separated lines, means for filtering the EUV pulses to obtain EUV pulses of a single spectral line, means for irradiating a specimen to be analyzed with the filtered EUV pulses, a flight channel for passage of photoelectrons emitted from the specimen irradiated with the EUV pulses, and electron current measurement means for measuring a distribution of flight time of the photoelectrons.

A laser plasma produced by irradiating a solid target with a pulsed laser beam is a compact and extremely high brilliance X-ray and EUV source. If this source is available, a compact and high-efficiency electron spectroscopy apparatus that is capable of performing high spatial resolution measurements in a short time will be realized. While there have been quite numerous works on the application of laser plasmas to X-ray lithography, however, there has been no discussion on the possibility of employing laser plasmas as a source of photoelectron spectroscopy. There are two major reasons for this; the spectroscopic structure of the emission from plasmas, and the low average emitting power.

As seen in FIG. 7 of Boiko et al.; J. Quant. spectrosc. Radiat. Transfer, 19 (1978) 11, a laser plasma emits numerous spectral lines. In photoelectron spectroscopy, however, a single spectral line of very narrow bandwidth is required, so that the spectroscopic structure of the emission from a plasma is unsuitable for photoelectron spectroscopy.

A laser plasma emits quite bright EUV pulses but lasts only for a few nanoseconds or so. Therefore, even at the highest repetition rate of 1 kHz, the accumulated emitting time after 300 hours operation is merely a few seconds, leading to very low average power. When compared with a huge scale synchrotron source in X-ray lithography, a laser plasma can find a way to exist as a compact substitute source. In photoelectron spectroscopy, however, an X-ray tube is already sufficiently compact and there would be no merit in using a laser plasma if there is not a good method for utilizing the pulse-nature of the source.

In the present invention, the above two problems regarding use of a laser plasma for photoelectron spectroscopy are solved as described below.

The first problem is solved by creating a laser plasma composed mainly of a single ion species emitting EUV pulses of a plurality of spectrally well-separated lines, and by filtering the EUV pulses to obtain EUV pulses of a single spectral line.

The second problem is solved by adopting the time-of-flight technique for the analysis of photoelectron energy.

Further features of the invention, its nature and various advantages will be more apparent from the accompanying drawings and following detailed description of the invention.

BRIEF DESCRIPTION OF THE DRAWINGS

FIG. 2 shows the general arrangement of an embodiment of the electron spectroscopy apparatus according to this invention; and FIG. 3 illustrates how to get a single spectral line from a laser plasma source, in which FIG. 3(a) shows a spectrum from a plasma comprising ions of various ionization stages, FIG. 3(b) a spectrum from a plasma composed mainly of a single ion species emitting line $S_1$ well-separated from other lines, and FIG. 3(c) the selection of a single emission line $S_1$ using a filter with the displayed transmission spectrum.

DESCRIPTION OF THE PREFERRED EMBODIMENT

Figure 1:
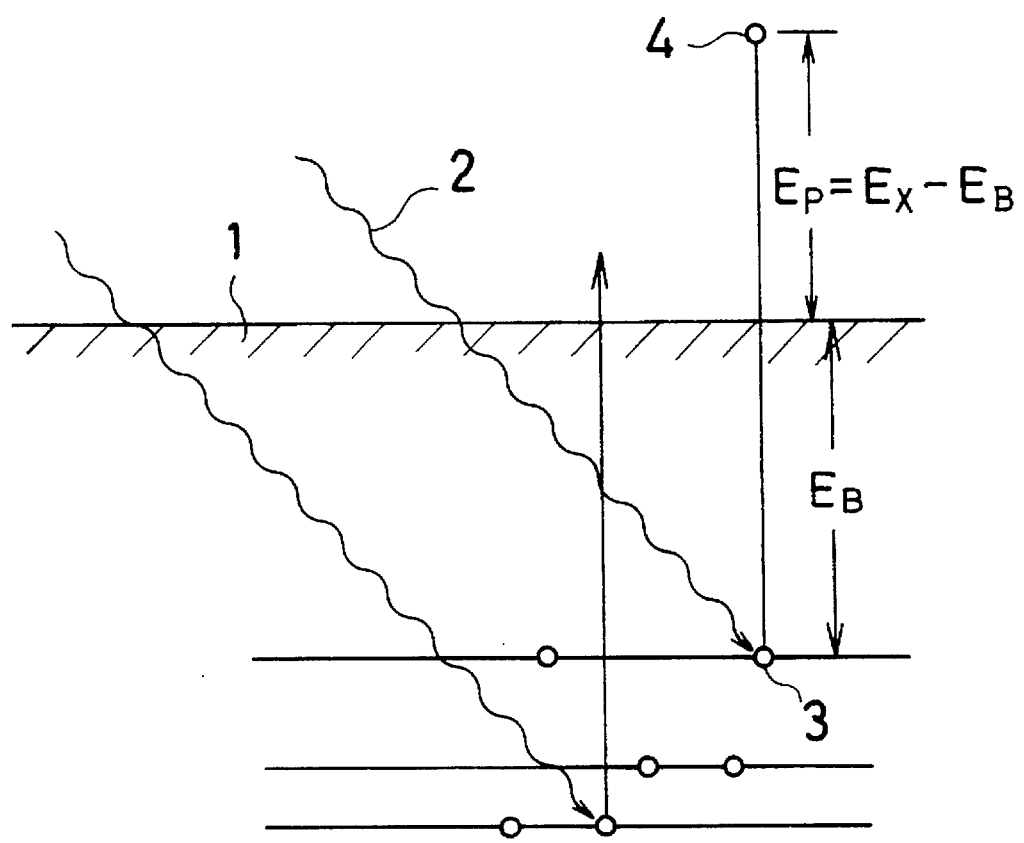
FIG. 1 is a diagram illustrating the principle of photoelectron spectroscopy.

The present invention will now be described with reference to the embodiment illustrated in FIG. 2, which comprises a laser device 11, a vacuum chamber 12 for EUV generation, a laser-beam focusing lens 13, a target 14, a target shaft 15, a laser plasma 16, a pulsed EUV beam 17, a pinhole 18 for limiting the diameter of the EUV source, an EUV guide channel 19, a high-vacuum chamber 20 for photoelectron measurement, an EUV focusing system 21, a measurement sample 23, an electron lens 24 for capturing electrons emitted over a wide angle range, photoelectrons 25, a retarding-field grid 26, a photoelectron flight channel 27, a photoelectron detector 28, a photoelectron-current time-waveform meter 29 and a photoelectron spectrum analyzer 30.

To enable rapid measurement, the laser device 11 uses a short-pulse laser with a high repetition rate of at least several tens of Hertz, and more preferably 1 kHz or more. As described below, when measuring photoelectrons by the time-of-flight method, in order to obtain sufficient energy resolution it is necessary to sufficiently reduce the time duration of the generated X-ray pulses, for which it is preferable that the irradiating laser pulse width does not exceed 2 ns or so. An energy per pulse of around 10 mJ or more is required. Focused power density of $10^{10}$ to $10^{13}$ W/$cm^2$ is required to generate EUV efficiently; in the case of pulses with a duration of 2 ns and an energy of 20 mJ, the laser-beam condenser lens 13 focuses the laser beam to a diameter of 10 to 300 μm on the target 14, producing plasma 16 that generates the pulsed EUV beam 17.

The material selected for the target 14 depends on which of the elements included in the measurement sample 23 is to be detected. The optimum EUV wavelength will vary depending on the detected element, but EUV of various wavelengths can be generated from the laser plasma, depending again on which material is selected. By changing the target material to generate EUV of wavelengths down to 1.3 nm, it is possible to perform photoelectron spectroscopy of all elements at the optimum wavelength. With 6-nm EUV, all elements can be detected although not at the optimum wavelength.

The laser plasma 16 can generate a pulsed EUV beam 17 that includes numerous sharp spectral lines having a width that is 1/1000 or less the wavelength. When a laser plasma is composed mainly of a single ion species, and if this ion species emits an emission line spectrally well-separated from other lines, a single line for electron spectroscopy can be selected from among the lines. How a single line is selected is explained with reference to the schematically illustrated spectra in FIG. 3.

Generally, a laser plasma is composed of ions of various ionization stages. Each ion emits many lines, and the spectroscopic structure is too complicated to enable selection of a single line, as shown in FIG. 3(a). However, if a laser plasma is created to be composed mainly of a single ion species by the precise control of laser irradiation, there could exist an emission line spectrally well-separated from other lines as shown by $S_1$ in FIG. 3(b). A spectrally well-separated line such as $S_1$ in FIG. 3(b) makes it possible to select a single line by use of a filter having a poor wavelength resolution as shown in FIG. 3(c).

The degree of "well-separation" of the line depends on the resolution of the filter. If a multi-layered mirror is employed to select a single line, the line is required to be separated by more than 3% of the wavelength, because the resolution of the multilayers is only a few percent. (Trail et al., Appl. Phys. Lett., vol. 52 pp 269–271 (1988)). Often, it is not necessary for the filter to have only a single line within its transmission window. Even when two lines $S_1$ and $S_2$ in FIG. 3(b) are selected out by the filter, it will be easy to obtain real spectra from the observed photoelectron spectra by de-convoluting the effect of having two lines for exciting Photoelectrons.

Good candidate ions for generating well-separated lines are ions having a hydrogen-like, helium-like, or neon-like electron configuration. While there are cases where well-separated spectral lines are provided even when a plasma is composed of ions of various ionization stages, for easier selection of a single spectral line a laser plasma is strongly desired to be composed mainly of a single ion species.

Examples of spectral lines to be obtained are 16-nm line from Ne-like aluminum, 13.5-nm line from hydrogen-like lithium, 12-nm line from Ne-like silicon, 6nm line from helium-like boron, and 4-nm line from helium-like carbon.

Precise controlling of laser irradiation conditions makes it possible to produce a plasma composed of a small number of ion species. In fact, Tomie et al. found that emission spectra from germanium plasmas produced by the irradiation of a 10 ps KrF laser pulse at $8\times10^{13}$ W/cm$^2$ changed dramatically when quite low intensity prepulse of $4\times10^{10}$ W/cm$^2$ preceded the main pulse, and that the plasma produced with the prepulse was found to be composed mainly of Ne-like germanium ions from the analysis of the spectrum.

It is known that various parameters, such as the laser irradiation power density, laser wavelength, pulse width, power density of prepulse, target shape and so on, change the characteristics of plasmas. Therefore, there is no single specification of irradiation conditions for creating a plasma composed mainly of a single ion species. Rather, optimum irradiation conditions should be found through observation of plasmas. Ion species in a laser plasma can be determined by observing detailed X-ray spectra emitted from the plasma, and identifying the origin of lines.

The target 14 may be of any element that can be obtained. If it is easy to obtain as a pure material as in the case of aluminum, a target may be used that is formed of just that one element. If an element can be obtained in solid form only as a compound, such as the nitrogen in BN, then that compound may be used for the target. If the target 14 material can be obtained cheaply in rod form, such as in the case of aluminum, the rod can be used in that form as the target shaft 15. If the material is costly such as gold, or for any reason cannot be obtained as rod, the material may be used in powder form, coated on the target shaft 15, or as foil or sheet wound around the target shaft 15. The irradiation by pulses of laser light inflicts damage on the target 14, so the target 14 is rotated on the target shaft 15 so that a fresh portion of the target surface receives the irradiation. The target 14 may be in the form of a tape that can be advanced instead of the target shaft 15 arrangement.

The vacuum chamber 12 and the high-vacuum chamber 20 are optically connected by the EUV guide channel 19. The vacuum of the vacuum chamber 12 should be low enough to ensure that the EUV are not attenuated before reaching the chamber 20, for example around 0.1 pascal or below. On the other hand, for photoelectron spectroscopy on a clean surface of a solid, a high vacuum of $10^{-8}$ pascals or below should be used for the chamber 20 to avoid contamination of the surface.

In order to collect as much as possible the EUV which are emitted nearly isotropically from the laser plasma 16, the inlet of the EUV focusing system 21 should have as large a diameter as possible. As shown, the EUV focusing system 21 consists of a Schwarzschild type reflector by a pair of concentrically arranged spherical mirrors 22a and 22b, thereby forming an optical system that uses normal-incidence reflection can be provided with a large-diameter inlet and is able to concentrate the beam down to a sufficiently small diameter.

A multilayer coating is formed by deposition on the surfaces of the spherical mirrors 22a and 22b to efficiently concentrate the EUV. It is possible to have multilayer coatings that provide a normal-incidence reflectivity of 70 percent for EUV of a 7 nm or longer wavelength. A Schwarzschild type objective consisting of a combination of two mirrors having a relatively narrow reflection spectrum window also serves as a spectrometer. This can be utilized to select a single spectral line out of the many lines in the pulsed EUV beam 17 generated by the plasma 16 as explained in FIG. 3(c). The irradiation of the measurement sample 23 by a single-line of narrow width makes it possible to carry out photoelectron spectroscopy with a high energy resolution. An EUV beam with a smaller diameter on sample 23 can be obtained by using the pinhole 18 to limit the size of the EUV source.

Photoelectrons 25 produced by the EUV irradiation of the measurement sample 23 are passed through the photoelectron flight channel 27 to convert the photoelectron energy spectrum to electron-current temporal profile. In the time-of-flight method, the photoelectron energy resolving power is limited by the width of the EUV beam pulses 17. To take an example, an electron with an energy of 50 eV will travel 45 cm in 100 ns, and if the pulse width of the EUV beam 17, that is, the initial duration of the electron stream, is 1 ns, the time resolution will be 1 percent and the energy resolution 2 percent, leading to a resolving power of 1 eV.

Compared with a cylindrical mirror analyzer (CMA) or a spherical sector analyzer (SSA) employed in conventional electron spectroscopy, in which electrons having the energy within a specified energy window are detected in one measurement and a spectrum is achieved by scanning the energy position of the detection window, time-of-flight technique is a very high efficient electron detection method because all electrons having different energies are recorded in one detection and because electrons emitted into wide angles can be collected by an electron lens. Because a laser plasma is a pulsed source in its nature, the time-of-flight -technique can be adopted, and the high-efficiency of the technique can compensate for the low averaging power of the laser plasma source.

The photoelectron flight channel 27 may be arranged as a concentric copper tube with a gold-coated inner surface and wound with a solenoid coil to reduce stray electromagnetic field interfering with the flight of photoelectrons. The length of the photoelectron flight channel 27 will depend on the required photoelectron energy resolution and on how easy it is to fabricate the channel. For example, with EUV pulses in the order of nanoseconds and a time resolution of around 1 percent, a flight time in the order of 100 ns is required. Therefore, assuming a photoelectron energy of several tens of electron volts, a length of 20 to 100 cm would be appropriate for the photoelectron flight channel 27.

Providing a retarding-field grid 26 at the inlet of the photoelectron flight channel 27 to apply a retarding field can produce a major improvement in the energy resolution of photoelectron spectrum. For example, photoelectrons 25 emitted from the specimen with an energy of 50 eV that are passed through a −40 V retarding field will be retarded to 10 eV. As a result, the time-off-light in the photoelectron flight channel 27 will be lengthened to 224 ns and the energy resolution will be 0.09 eV. Photoelectron spectroscopy with a very high energy resolution can be achieved by adjusting the strength of the retarding field. This retardation method reduces the range of photoelectron energies that can be measured, so a measurement procedure is employed which starts with the measurement of the whole energy spectrum, without using any retarding field, and this is followed by the adjustment of the retarding field and high energy resolution measurement at the required point of the spectrum.

A multichannel plate is used for the photoelectron detector 28 that measures the time-of-flight of photoelectrons in the photoelectron flight channel 27. This is done to provide a high enough sensitivity to enable single electrons to be detected, to achieve a high-speed response in the order of nanoseconds, and to capture photoelectrons emitted in a wide solid angle. There are cases in which information relating to the electronical state of a substance can be obtained from the angular distribution of emitted photoelectrons. In such a case, a small-diameter multichannel plate is used or photoelectrons are passed through a small pinhole for detection, to detect only photoelectrons emitted within a narrow angular range. The emission angle distribution of the photoelectrons can be obtained by sweeping the angular detection positions or by arranging detectors at various angular positions.

In the many cases in which information on the distribution of the emission angle is not required, measurement can be speeded up by measuring photoelectrons collected over the broadest possible angular range. This can be done either by increasing the detection area of the photoelectron detector, or by using a photoelectron lens 24 that has the ability to concentrate electrons.

In the electron spectroscopy apparatus having the configuration described above, a target 14 that generates EUV of a specific wavelength is mounted on the target shaft 15 which is rotated, and pulses of laser light generated by the laser device 11 are focused onto the rotating target by the laser-beam focusing lens 13 to thereby produce plasma 16 and generate a pulsed EUV beam 17. The pulsed EUV beam 17 enters the high-vacuum chamber 20 via the EUV guide channel 19, and a single line spectrally well-separated from many other lines in the EUV pulse 17 is selected and focused onto a measurement sample 23 by the Schwarzschild focusing optics coated with a multilayer. A portion of the photoelectrons 25 emitted from the measurement sample 23 as a result of the EUV irradiation fly along the photoelectron flight channel 27 and are detected by the photoelectron detector 28. The photoelectron spectrum at the point at which the specimen is irradiated by the pulses of EUV is obtained from the analysis by the photoelectron spectrum analyzer 30 of the temporal profile of the photoelectron current recorded by the photoelectron-current time-waveform meter 29. The spatial distribution of the energy spectrum is obtained by scanning the location at which the EUV are converged on sample 23. The energy resolving power can be raised by retardation of the photoelectrons 25 by the application of a field generated by the retarding-field grid 26. With the aim of decreasing the required measurement time an increased number of the photoelectrons 25 emitted from the measurement sample 23 can be directed into the photoelectron flight channel 27 by arranging an electron lens 24 in front of the photoelectron flight channel 27.

When an intermittent phenomenon such as the generation of clusters is to be observed by synchronizing the irradiation of the target 14 by pulses of laser light from the laser device 11, the generation of the pulsed EUV 17 can be synchronized with said phenomena. The same method described above can be used for measuring the photoelectron energy spectra.

What is claimed is:

1. An electron spectroscopy apparatus, comprising:

means for generating EUV pulses using a laser plasma composed mainly of a single ion species produced by the irradiation of a pulsed laser beam on a solid target containing a specific element, said single ion species emitting EUV pulses of a plurality of spectrally well-separated lines;

means for filtering said EUV pulses to obtain EUV pulses of a single spectral line;

means for irradiating a specimen to be analyzed with said filtered EUV pulses;

a flight channel for passage of photoelectrons emitted from said specimen irradiated by said EUV pulses; and electron current measurement means for measuring a distribution of flight time of said photoelectrons.

2. An electron spectroscopy apparatus according to claim 1, wherein said means of filtering said EUV pulses includes multilayered mirrors.

3. An electron spectroscopy apparatus according to claim 2 further comprising means for focusing said EUV pulses onto said specimen.

4. An electron spectroscopy apparatus according to claim 3, wherein said EUV focusing means includes Schwarzschild type optics concurrently serving as said means for filtering said EUV pulses.

5. An electron spectroscopy apparatus according to claim 1 further comprising means for focusing said EUV pulses onto said specimen.

6. An electron spectroscopy apparatus according to claim 5, wherein said EUV focusing means includes Schwarzschild type optics concurrently serving as said means for filtering said EUV pulses.

7. An electron spectroscopy apparatus according to claim 1, wherein said flight channel is provided with means for retarding the speed of said photoelectrons.

8. An electron spectroscopy apparatus according to claim 1, further comprising means for collecting said photoelectrons emitted from said specimen.

9. An electron spectroscopy apparatus according to claim 1, wherein said laser plasma is composed mainly of ions having an H-like electron configuration.

10. An electron spectroscopy apparatus according to claim 9, wherein said ions are H-like lithium ions.

11. An electron spectroscopy apparatus according to claim 1, wherein said laser plasma is composed mainly of ions having an He-like electron configuration.

12. An electron spectroscopy apparatus according to claim 10, wherein said ions are one member selected from the group consisting of He-like boron ions and He-like carbon ions.

13. An electron spectroscopy apparatus according to claim 1, wherein said laser plasma is composed mainly of ions having an Ne-like electron configuration.

14. An electron spectroscopy apparatus according to claim 13, wherein said ions are one member selected from the group consisting of Ne-like aluminum ions and Ne-like silicon ions.

* * * * *